US006441622B1

(12) United States Patent
Wrzesinski et al.

(10) Patent No.: US 6,441,622 B1
(45) Date of Patent: Aug. 27, 2002

(54) METHOD AND APPARATUS FOR TIME DOMAIN REFLECTOMETRY MOISTURE SENSING IN VARIOUS MEDIA

(75) Inventors: Stanley Wrzesinski, Arlington Heights; Daniel A. Young, Gurnee, both of IL (US)

(73) Assignee: Motorola, Inc., Schaumburg, IL (US)

( * ) Notice: Subject to any disclaimer, the term of this patent is extended or adjusted under 35 U.S.C. 154(b) by 10 days.

(21) Appl. No.: 09/641,786

(22) Filed: Aug. 18, 2000

(51) Int. Cl.$^7$ .................... G01R 27/32; G01R 31/11; H01Q 7/08
(52) U.S. Cl. ................ 324/643; 324/533; 324/640; 324/694; 343/788
(58) Field of Search ................ 324/643, 629, 324/642, 640, 694, 533, 529; 340/605; 343/719, 788

(56) References Cited

U.S. PATENT DOCUMENTS

| | | |
|---|---|---|
| 4,341,112 A | 7/1982 | Mackay et al. |
| 4,389,900 A | 6/1983 | Gutierrez |
| 4,850,386 A | 7/1989 | Bireley |
| 4,918,375 A | 4/1990 | Malicki et al. |
| 5,260,666 A | 11/1993 | Dishman |
| 5,341,673 A | 8/1994 | Burns |
| 5,479,104 A | 12/1995 | Cambell |
| 5,609,059 A | 3/1997 | McEwan |
| 5,648,724 A | 7/1997 | Yankielun et al. |
| 5,723,979 A | 3/1998 | Mohr |
| 5,818,241 A * | 10/1998 | Kelly ................ 324/640 |
| 6,281,801 B1 * | 8/2001 | Cherry et al. ......... 324/643 |

OTHER PUBLICATIONS

Topp, G.C., Davis, J.L.; "Measurement of Soil Water Content using Time–Domain Reflectometryry (TDR): A Field of Evaluation", Soil Science Society AM. Journal, vol. 49, 1985.

Dasberg, S., Dalton, F.N., "Time Domain Reflectometry Field Measurements of Soil Water Content and Electrical Conductivity," Soil Science Society AM. Journal, vol. 49, 1985.

Topp, G.C.; "Electromagnetic Determination of Soil Water Content: Measurements in CoAxial Transmission Lines;" Water Resources Research, vol. 16, No. 3, pp. 574–582, 1980.

* cited by examiner

Primary Examiner—N. Le
Assistant Examiner—Anjan K. Deb
(74) Attorney, Agent, or Firm—Gary J. Cunningham; Thomas V. Miller

(57) ABSTRACT

A method and apparatus for time domain reflectometry sensing of moisture in a test material. The sensor (200) having a generally helical shaped electrode (206) and at least one secondary electrode (208) spaced apart from the generally helical shaped electrode (206) to enable the test material to be present in the space (210) between the helical shaped electrode (206) and the secondary electrode (208). A wave pulse generator (202) is coupled to the generally helical shaped electrode (206) and the secondary electrode (208) that results in a reflection of the generated wave from the wave pulse generator (202). Additionally, a reflected pulse detector (204) is coupled to the generally helical shaped electrode (206) and the secondary electrode (208), in which the reflected wave pulse detector (204) receives a reflected wave pulse from the wave pulse generator (202). A controller that activates the wave pulse generator (202) also controls a counter (114) that records the delay between the generated wave pulse and reflected wave pulse from which the moisture content of the test material (212) is determined.

20 Claims, 4 Drawing Sheets

METHOD AND APPARATUS FOR TIME DOMAIN REFLECTOMETRY MOISTURE SENSING IN VARIOUS MEDIA

FIELD OF THE INVENTION

The present invention relates generally to moisture sensors and, specifically to, time domain reflectometry moisture sensors.

BACKGROUND OF THE INVENTION

The use of time domain reflectometry has been previously known as a method for determining the level of liquids in tanks and other enclosures. Furthermore, time domain reflectometry sensors are used to measure moisture in various media via high velocity wave propagation. The velocity of the wave propagation in a time domain reflectometry sensor is on the order of one nano-second per foot. In order to process the wave propagation at such velocity, high speed electronics are required in a wave detector circuit. Another approach to processing the wave propagation through a media involves high speed retriggering excitation wave pulses upon detection of the reflected wave pulse resulting in a continuous oscillator function where the frequency represents the state of the media being measured.

The problems with the above approaches are that high speed electronics increase the product cost of the time domain reflectometry moisture sensor and a continuous frequency of an oscillator function needs to be divided into measurable parameter. Accordingly, there is a need in the art for a time domain reflectometry functioning as a liquid sensor that does not require high speed electronics in the wave detector.

DETAILED DESCRIPTION

To overcome the problems caused by the high velocity wave propagation, embodiments of the method and apparatus for a time domain reflectometry sensor are described in which the wave propagation velocity is slowed to enable a measurement in the time domain. Furthermore, the slower propagation of the wave allows lower speed circuitry such as CMOS or HCMOS to be used while still maintaining measurements in the time domain.

The principle of time domain reflectometry is based on physics describing wave propagation through any media. The wave propagation equations are function of permitivity and permeability of the media. The basic equation for velocity is;

$$v = \frac{1}{\sqrt{(\mu * \epsilon)}},$$

where
  $v$=Velocity,
  $\mu$=Permeability of the media,
  $\epsilon$=Dielectric constant of the media,
and characteristic impedance of the wave will have an impedance of;

$$\eta = \sqrt{\frac{\mu}{\epsilon}},$$

where
  $\eta$=Impedance
Both of the equations above have an electrical equivalent where velocity is;

$$v = \frac{1}{\sqrt{(L * C)}},$$

where
  $v$=Velocity,
  L=Inductance,
  C=Capacitance,
and the characteristic impedance is;

$$z_0 = \sqrt{\frac{L}{C}},$$

where
  $z_0$=Impedance,
  L=Inductance,
  C=Capacitance.

Thus, high permeability magnetic materials (i.e. ferrous material) with high permitivity can, in some transmission line configurations, slow down the propagation velocity by at least the second order factors by taking advantage of the above relationships between velocity, inductance, and capacitance. Furthermore, the delay in the time domain reflectometry moisture sensor is introduced by the effects of generally helical or annular wound structures such as a helix or a spiral. A generally helical structure is typically a conductors wound about an axis at a fix or variable distance.

Figure 1:
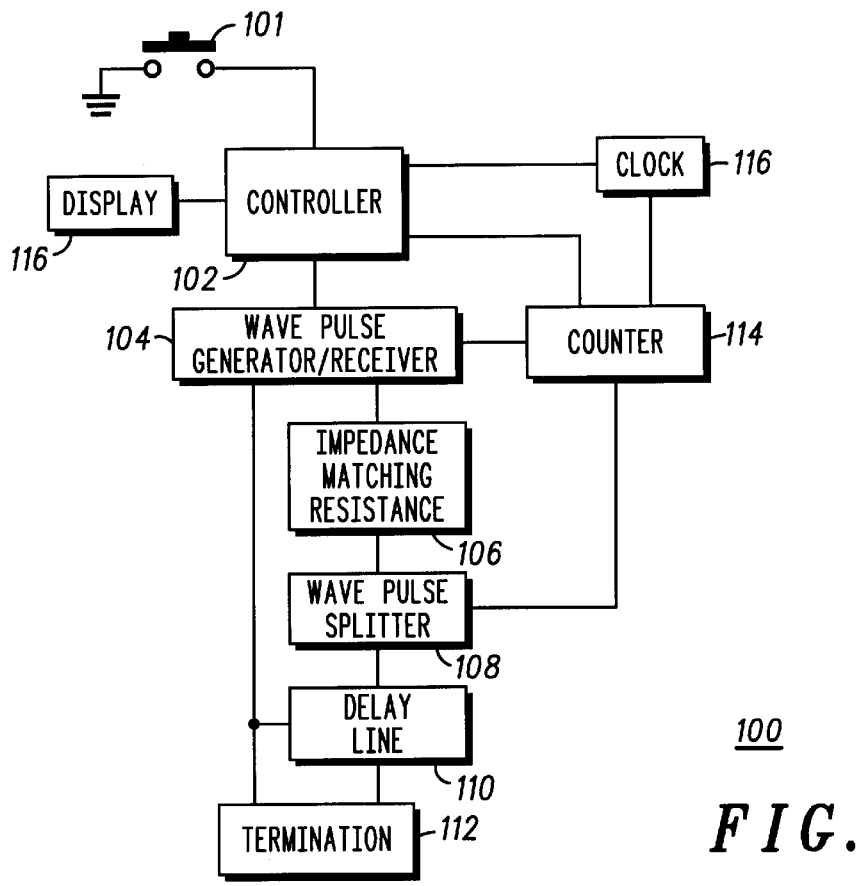
FIG. 1 is a block diagram of a time domain reflectometry sensor in accordance with an embodiment of the invention.

Turning to FIG. 1, a block diagram of a time domain reflectometry 100 is shown. A controller 102 is coupled to a trigger 101 a wave pulse generator/receiver 104, a counter 114, and a clock 116. In an alternate embodiment the trigger 101 may be implemented using automatic triggering circuits rather than a manual trigger 101. The wave pulse generator/receiver 104 is coupled to the controller 102, an impedance matching resistance 106, a termination 112, and a counter 114. The impedance matching resistance 106 is coupled to the wave pulse generator/receiver 104, and a wave pulse splitter 108. The delay line 110 is coupled to the wave pulse splitter 108, the wave pulse generator/receiver 104, and the termination 112. The wave pulse splitter 112 is coupled to the impedance matching resistance 106, the delay line 108 and the counter 114. The clock 116 is coupled to the controller 102 and the counter 114.

Upon activation of switch 101, the controller activates the wave pulse generator/receiver 104. The wave pulse generator/receiver 104 generates a wave pulse having a propagation delay greater than ten nano-seconds. The wave pulse transitions through the impedance matching resister 106 that matches impedance of the line impedance (i.e. the material carrying the wave transmission). By matching the line impedance, the impedance matching resister 106 eliminates multiple echo wave pulses.

The wave pulse travels from the impedance matching resistance 106 to the wave pulse splitter 108. The wave splitter 108 splits the wave pulse into a wave pulse that activates the counter and another wave pulse that is sent to the delay line 110 (i.e. a forward traveling pulse and a returning pulse).

The delay line 110 delays or slows the wave pulse. In one embodiment, the delay line is a generally helical electrical conductive path with a predetermined number of turns (e.g. 48 turns). In another embodiment, the structure may be two-dimensional that is selectively encased in a ferrous material. Additionally in other alternate embodiments, other material having a high permeability value that can slow the propagation of the wave pulse may selectively be used instead of ferrous material.

The delay line 110 is coupled to the termination 112. The termination 112 is shorted in the present embodiment and results in a reflected wave having an inverted magnitude (the wave pulse is inverted). In an alternate embodiment, the termination 112 is an open circuit and results in the doubling of the wave pulse amplitude.

The wave pulse creates a potential difference between the delay line 110 acting as a capacitor formed by two electrodes (shown in FIG. 2) separated by the material being measured. The material being measured is the dielectric in the capacitor.

The received wave pulse is detected by the wave pulse generator/receiver 104 and results in the halting of the counter 114. The count recorded by the counter 114 is accessed by the controller 102 and the moisture content of the sampled material is calculated and displayed on display 116 (i.e. LCD display, CRT, or other visual or audio indicators). Thus, the wave pulse propagation velocity is reduced as it travels through the delay line 110. The slower reflected wave pulse enables CMOS or HCMOS logic chips to be used in the wave pulse receiver circuitry. The use of CMOS or HCMOS circuitry (or there means able to detect the slower reflected wave) results in a cost savings over the use of more expensive high speed logic chips that traditionally have been used in time domain reflectometry sensors.

Figure 2:
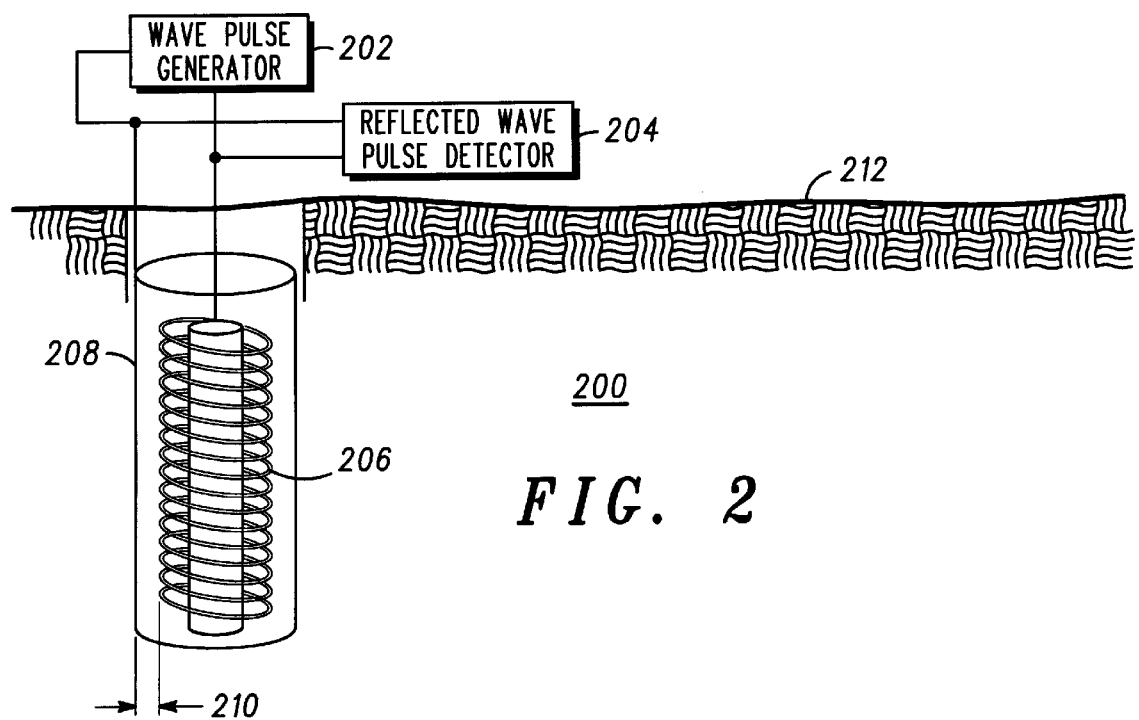
FIG. 2 is a diagram of a generally helical time domain reflectometry sensor measuring soil moisture in accordance with an embodiment of the invention.

In FIG. 2, a diagram of a generally helical time domain reflectometry sensor 200 for detecting soil moisture is shown. A wave pulse generator 202 is coupled to a reflected wave pulse detector 204, a helical conductor 206, and an electrically conductive tube 208. A space 210 is created between the helical conductor 206 and the electrically conductive tube 208 that receives test material such as soil 212. The time domain reflectometry moisture sensor 200 is shown planted in soil 212.

The wave pulse generator 202 creates a wave pulse that is transmitted through the helical conductor 206. The helical conductor 206 slows the propagation of the wave pulse through the soil contained in the space 210 between the helical conductor 206 and the electrically conductive tube 208. The soil contained in the space 210 is a dielectric in the capacitor formed by the helical conductor 206 and the electrically conductive tube 208.

The reflected wave pulse is detected by the reflected wave pulse detector 204. A control circuit as shown in FIG. 1 is used to calculate the moisture content of the soil 212 upon determination of the time required for the propagation of the wave pulse to be detected by the reflected wave pulse detector 204.

Figure 3:
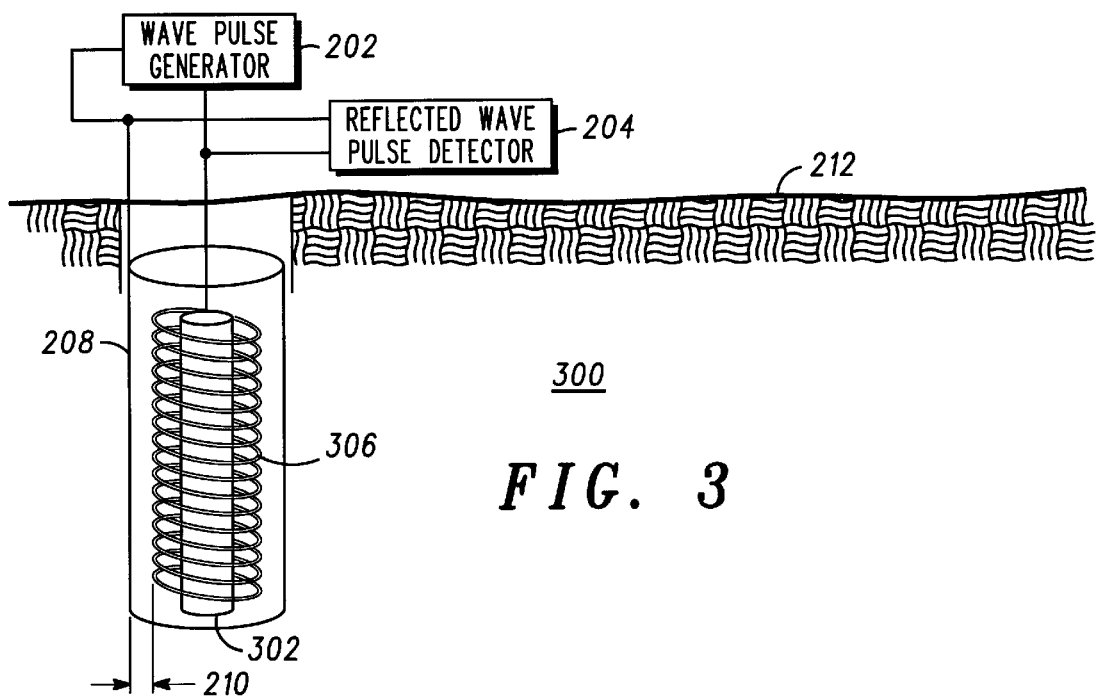
FIG. 3 is a diagram of a generally helical time domain reflectometry sensor having a ferrite rod for measuring soil moisture in accordance with an embodiment of the invention.

Turning to FIG. 3, a diagram of a generally helical time domain reflectometry sensor 300 having a ferrite rod 302 for measuring soil moisture is shown. A wave pulse generator 202 is coupled to a reflected pulse detector 204, a helical wound conductor 306, and an electrically conductive tube 208. The helical wound conductor 306 is supported by a ferrite rod 302 (helical wound conductor 306 wrapped around the ferrite rod 302). A space exist 210 between the helical conductor 306/ferrite rod 302 assembly and the electrically conductive tube 208 for receiving test material such as soil 212. Furthermore, the time domain reflectometry moisture sensor 300 is shown planted in soil 212. Furthermore, the time domain reflectometry moisture sensor 300 is shown planted in soil 212.

The wave pulse is generated by the wave pulse generator 202 and is transmitted through the time domain reflectometry sensor as discussed in FIG. 2. In FIG. 3, the ferrite rod 302 is wrapped by the helical wound conductor 306 resulting in a further reduction in the wave propagation velocity as compared to the reduction caused by the helical wound conductor 206, FIG. 2.

Figure 4:
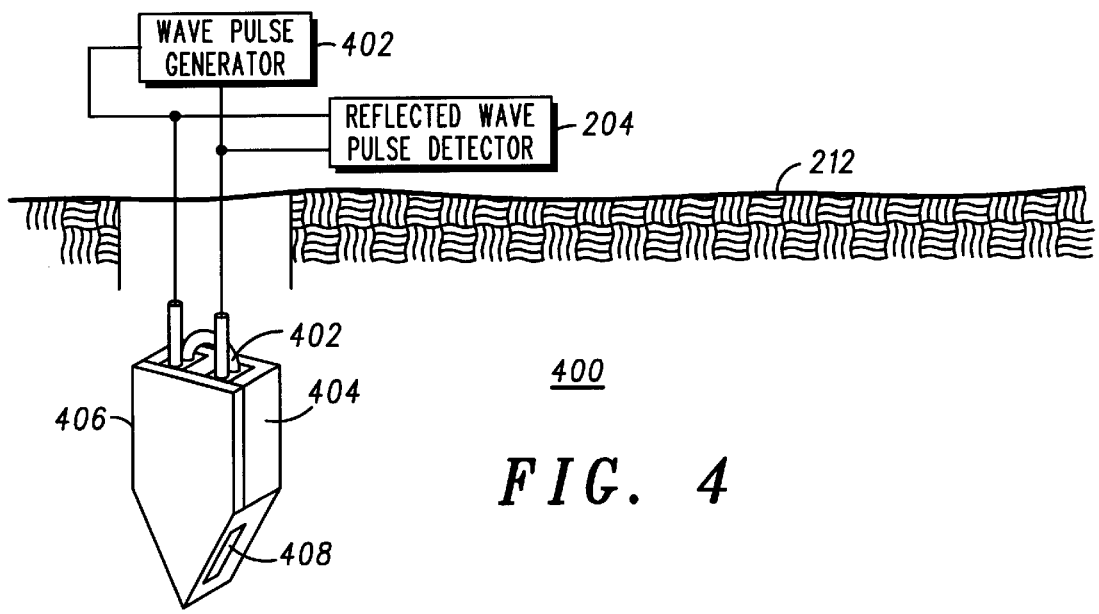
FIG. 4 is a diagram of a time domain reflectometry sensor contained in a ferrite enclosure for measuring soil moisture in accordance with an embodiment of the invention.

Turning to FIG. 4, a block diagram of a time domain reflectometry sensor 400 contained in an E-I ferrite enclosure 404 ("E" part), 406 ("I" part) for measuring soil moisture is shown. A balanced wave pulse generator 402 is coupled to a reflected pulse detector 204 and a wound conductor 402. The conductor 402 is a single turn or multiturn winding around a E-I ferrite structure 404, 406. The ferrite structure 404 contain air gap windows 408 that allow then entry of soil 212. The wound conductor 402 along with the ferrite E-I structure 404, 406 functioning as another electrical conductor are at least partially separated by soil 212 that enters one or more air gaps 408 in the ferrite E-I structure 404, 406. The soil 212 is a dielectric in a capacitor crated by the E-I structure 404, 406, helical conductor 402, and the dielectric (soil). The capacitor creates a measurable delay in the wave pulse propagation as previously discussed. The measurable delay is used to calculate the amount of moisture in the soil 212 or other test material. Additionally, an advantage of this embodiment is the ability to shape the ferrite structure 404, 406 to function as a stake for insertion into the soil 212.

Figure 5:
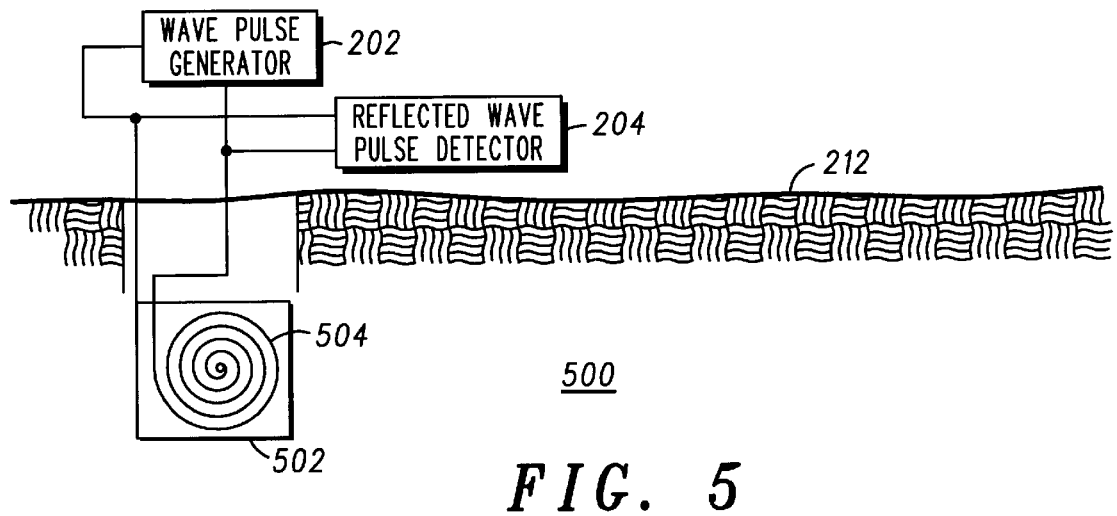
FIG. 5 is a diagram of a two-dimensional helical or spiral time domain reflectometry sensor embedded in a ferrite structure for measuring soil moisture in accordance with an embodiment of the invention.

In FIG. 5, a diagram of a two-dimensional helical time domain reflectometry sensor 500 embedded in a ferrite structure for measuring soil moisture is shown. A wave pulse generator 202 is coupled to a reflected wave pulse detector 204, a conductive plane 502, and a two-dimensional helical conductor 504.

The two-dimensional helical wound conductor 504 is a spiral shaped conductor embedded in ferrite and spaced apart from the conductive plane 502 with only the center of the spiral conductor 504 contacting the conductive plane 502 (i.e. shorted conductors having an inverted reflected wave pulse). The space between the spiral conductor 504 and the conductive plane 502 is filled with soil 212. The soil 212 is a dielectric in the capacitor created by the conductive plate 502 and the spiral wound conductor 504. As a result of the shape of the conductor 504, the wave pulse propagation velocity of the generated wave pulse is slowed. The wave propagation is further reduced by the ferrite material in which the spiral conductor 504 is embedded. The wave pulse generation and reflected wave pulse detection and the moisture content calculation using a counter occur as previous described.

Figure 6:
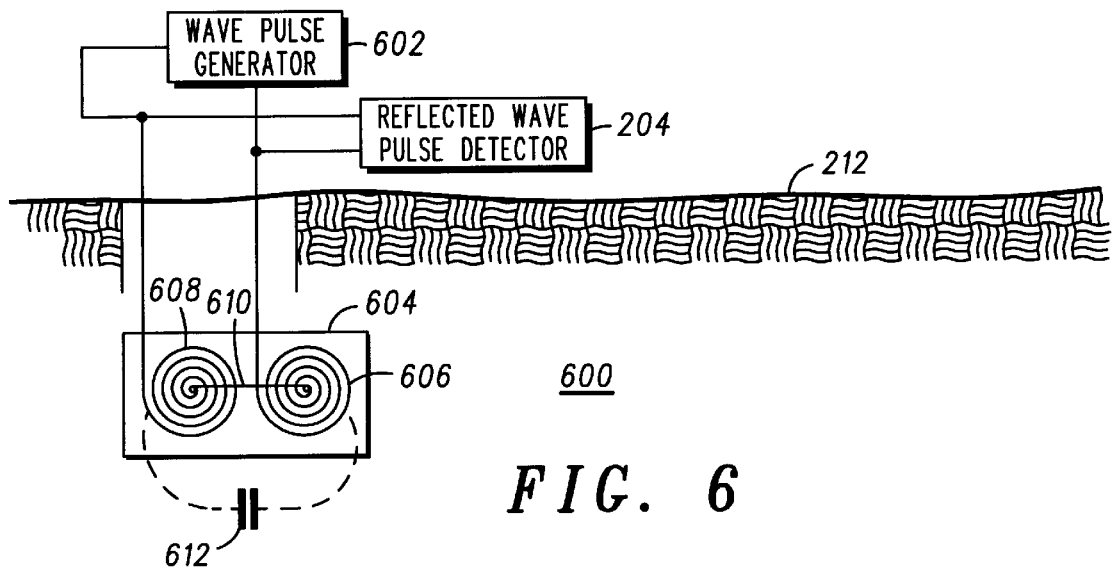
FIG. 6 is a diagram of a two-dimensional helical or spiral time domain reflectometry sensor embedded in a ferrite structure for measuring soil moisture in accordance with an embodiment of the invention.

In FIG. 6, a diagram of a two-dimensional helical or spiral time domain reflectometry sensor 600 embedded in a ferrite structure 604 for measuring soil moisture is shown. A balanced wave pulse generator 602 having a floating type termination or termination where return current is not grounded or connected to the chassis of the instrument is coupled to the reflected wave pulse detector 204, and two spiral conductors 606, 608. The two spiral conductors 606 and 608 are shorted together by connection 610.

Capacitance 612 is formed between the area of the spiral conductors 606, 608 and the dielectric properties of the soil 612 in response to the generated wave pulse. The delay of the reflected pulse is the result of the propagation velocity of the generated wave pulse and the dielectric properties of the soil 212. Moisture in the soil 212 affects the dielectric properties of the soil 212 and results in an increased time interval between the generated and reflected wave pulses as measure by the reflected wave pulse detector 204.

Figure 7:
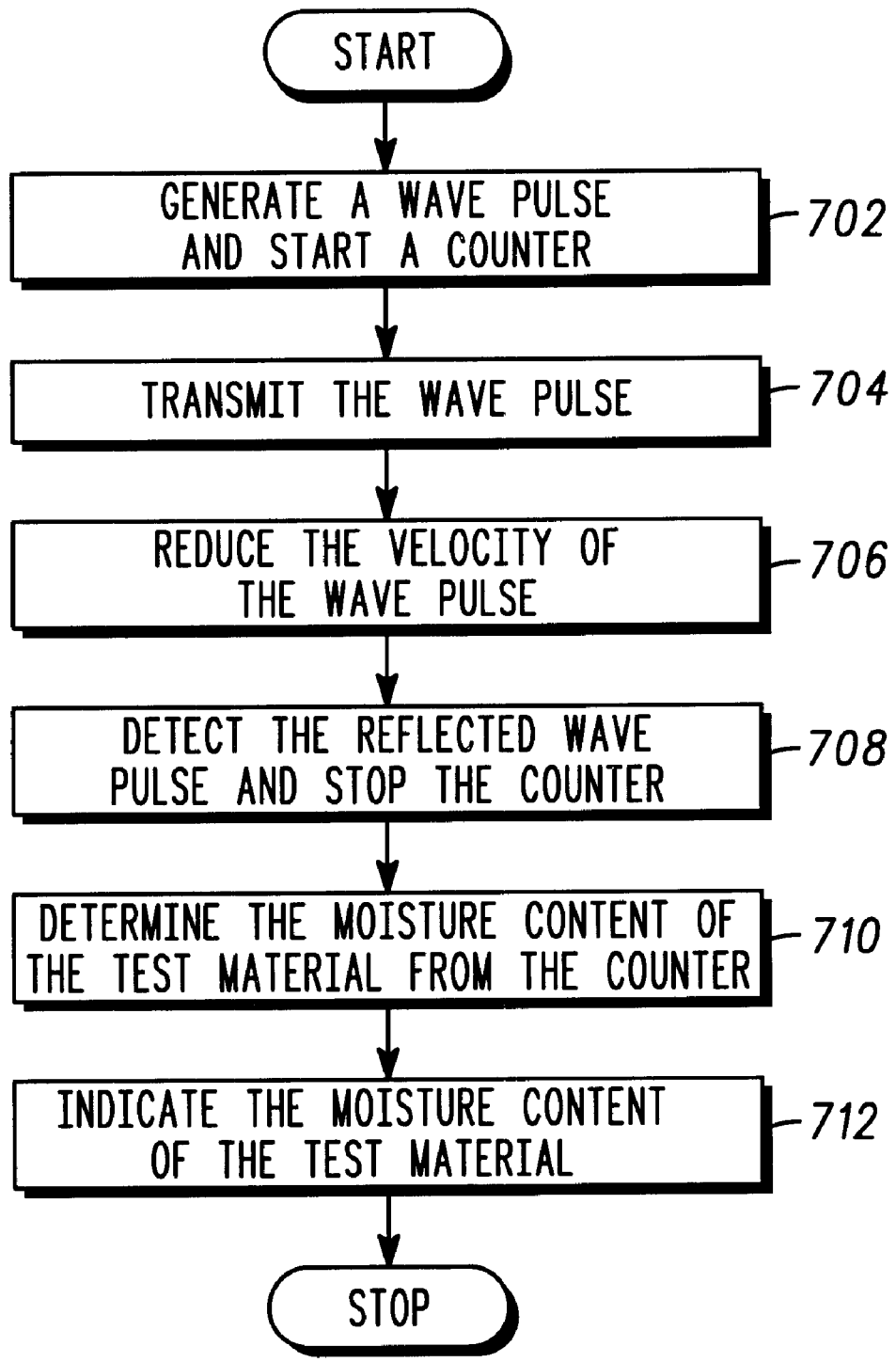
FIG 7 is a flow diagram of the steps of time domain reflectometry sensing in accordance with an embodiment of the invention.

Turning to FIG. 7, a flow diagram of the steps of time domain reflectometry sensing are shown in accordance with an embodiment of the invention. In step 702, the wave pulse generator/receiver 104, FIG. 1, receives an activation from the controller 102 to generate a wave pulse and start a counter 114. The wave pulse is transmitted in step 704, FIG. 7, from the wave pulse generator/receiver 104, FIG. 1, to the delay line 110. The velocity of the wave pulse is reduced by the delay line 110 in step 706, FIG. 7. In step 708, the reflected wave is detected by the wave pulse generator/receiver 104, FIG. 1, and the counter is stopped. The moisture content of the test material that acted as the dielectric in a capacitor is determined from the value of the counter 114 in step 710, FIG. 7. In step 712, the resulting moisture content value of the test material is indicated.

While the invention has been particularly shown and described with reference to a particular embodiment, it will be understood by those skilled in the art that various changes in form and details may be made therein without departing from the spirit and scope of the invention and it is intended that all such changes come within the scope of the following claims.

What is claimed is:

1. A time domain reflectometry moisture sensor apparatus for the measurement of moisture in a test material, comprising:
    a generally helical shaped electrode;
    at least one secondary electrode spaced apart from the generally helical shaped electrode to enable the test material to be present between the helical shaped electrode and the secondary electrode;
    a wave pulse generator coupled to the generally helical shaped electrode and the at least one secondary electrode;
    a reflected pulse detector coupled to the generally helical shaped electrode and the at least one secondary electrode, in which the reflected pulse detector receives a wave pulse from the wave pulse generator; and
    a rod made of a high permeability magnetic material, the rod is encircled by the generally helical shaped electrode.

2. The apparatus according to claim 1, wherein the high permeability magnetic material has a permeability measurement greater than one-hundred.

3. The apparatus according to claim 1, wherein the high permeability magnetic material is a ferrous material.

4. The apparatus according to claim 1, wherein the at least one secondary electrode is a tube containing and spaced apart from the generally helical shaped electrode.

5. The apparatus according to claim 1, wherein the wave pulse detected by the reflected pulse detector has a frequency of less than a gigahertz.

6. The apparatus according to claim 1, wherein the test material is soil.

7. The apparatus according to claim 1, wherein the wave pulse generator is automatically activated upon detection of the wave pulse at the reflected pulse detector.

8. A method for measuring an amount of moisture in a test material, comprising the steps of:
    generating a wave pulse at a wave pulse generator;
    transmitting the wave pulse having a predetermined velocity;
    reducing the velocity of the wave pulse via an assembly, the assembly comprising a generally helical shaped electrode and a magnetic rod, wherein the rod is encircled by the generally helical shaped electrode; and
    receiving the wave pulse at a reflected wave pulse detector via at least one secondary electrode spaced apart from the assembly with the ability to have test material between the assembly and the at least one secondary electrode.

9. The method of claim 8, in which the magnetic rod has a permeability measurement greater than ten.

10. The method of claim 9, in which the magnetic rod is made of a ferrous material.

11. The method of claim 8, wherein the assembly is encircled by the at least one secondary electrode.

12. The method of claim 8, in which the step of receiving further comprises the step of slowing the wave to a frequency of less than a gigahertz.

13. The method of claim 8, further comprising the steps of determining a delay between the wave pulse and the reflected wave pulse, and
    calculating the amount of moisture in the test material.

14. The method of claim 13 in which the test material is soil.

15. A method for measuring an amount of moisture in a test material, comprising the steps of:
    generating a wave pulse at a wave pulse generator;
    transmitting the wave pulse having a predetermined velocity;
    reducing the velocity of the wave pulse via a generally flat spiral shaped electrode embedded within a magnetic structure; and
    receiving the wave pulse at a reflected wave pulse detector via at least one secondary electrode spaced apart from the generally flat spiral shaped electrode with the ability to have test material between the generally flat spiral shaped electrode and the at least one secondary electrode.

16. The method of claim 15, the magnetic structure is made of a material having a wave permeability measurement greater than 10000.

17. The method of claim 16, in which the magnetic structure is made of a ferrous material.

18. The method of claim 15, in which the step of receiving further comprises the step of slowing the wave to a frequency of less than a gigahertz.

19. The method of claim 15, further comprising the steps of determining a delay between the wave pulse and the reflected wave pulse, and
    calculating the amount of moisture in the test material.

20. The method of claim 19 in which the test material is soil.

* * * * *